United States Patent [19]
Rolf et al.

[11] Patent Number: 5,744,586
[45] Date of Patent: Apr. 28, 1998

[54] MANUFACTURING PROCESS FOR THE PRODUCTION OF PURIFIED TRANSFERRIN

[75] Inventors: John M. Rolf, Los Angeles; Akimasa Ohmizu, Arcadia; Shawn D. Latham, Sierra Madre; Prabir Bhattacharya, Walnut, all of Calif.

[73] Assignee: Alpha Therapeutic Corporation, Los Angeles, Calif.

[21] Appl. No.: 668,351

[22] Filed: Jun. 26, 1996

[51] Int. Cl.$^6$ .......................... A61K 38/00; C07K 5/00; C07K 7/00; C07K 16/00

[52] U.S. Cl. .......................... 530/394; 530/412; 530/416; 530/380; 530/395; 424/85; 514/8; 514/724

[58] Field of Search .......................... 530/394, 412, 530/416, 380, 395; 424/85; 514/724, 8

[56] References Cited

U.S. PATENT DOCUMENTS

| | | | |
|---|---|---|---|
| 4,540,573 | 9/1985 | Neurath et al. | 424/85 |
| 4,841,026 | 6/1989 | Van Beveren et al. | 530/394 |
| 5,041,537 | 8/1991 | Bethke et al. | 530/394 |

OTHER PUBLICATIONS

Harris, et al., Protein Purification Methods A Practical Approach, pp. 5–9, 126–148, 1989.

Soliman, et al., A Medium Scale Method for the Purification of Human Serum Transferrin and IgG Globulin by Chromatographic Technique, U.A.R. J. Chem., vol. 14, No. 2, pp. 177–183, 1971.

*Primary Examiner*—Cecilia J. Tsang
*Assistant Examiner*—Jennifer Harle
*Attorney, Agent, or Firm*—Sughrue, Mion, Zinn, Macpeak & Seas, PLLC

[57] ABSTRACT

Method for obtaining highly purified transferrin from a partially purified plasma fraction containing transferrin in which the starting fraction is concentrated. Its ionic strength is reduced and then transferrin is adsorbed onto a chromatographic column. Following elution, the transferrin can be further processed through to packaging in final containers. The final purified transferrin product is sterile, at least 95% pure and is substantially free of enveloped and non-enveloped viruses.

21 Claims, No Drawings

MANUFACTURING PROCESS FOR THE PRODUCTION OF PURIFIED TRANSFERRIN

FIELD OF THE INVENTION

The present invention relates to a process for the purification of transferrin resulting in a product adequate for medical uses.

BACKGROUND OF THE INVENTION

Transferrin is an iron-binding glycoprotein having a molecular weight of 76–81 kD. Iron-free transferrin is referred to as "apo-transferrin," whereas iron-saturated transferrin is referred to as "holo-transferrin." Both apo-transferrin and holo-transferrin are used for therapeutic purposes.

In blood plasma, transferrin acts as an iron-transport protein that safely sequesters trivalent iron as it is delivered to the cell cytoplasm via cell surface transferrin receptors. Central nervous system (CNS) neurons are deficient in transferrin receptors, while tumor cells commonly have an excess. A conjugate of transferrin and a protein or a small molecule may provide a useful treatment for CNS tumors by selective delivery to the targeted cells. Such proteins may include toxins. Such molecules may includes chemotherapeutic agents, radioisotopes and nucleic acids. For example, U.S. Pat. No. 5,352,447 discloses a conjugate of transferrin and diphtheria toxin for the treatment of intracranial lesions.

Several other medical applications also involve the use of purified transferrin products. For instance, transferrin products are used as cell growth factors in serum-free cell culture media. Purified transferrin products may also be used as reagents in diagnostic kits.

Therefore, there is a continuing need for highly purified and sterile transferrin products that are free of enveloped and non-enveloped viruses. Moreover, there is the need for the ability to make these highly purified products on an industrial scale in a simple and cost effective manner.

Fraction IV is often considered a waste product of the Cohn fractionation process. However, it is also known that Fraction IV contains a range of useful plasma proteins including albumin, alpha-1 proteinase inhibitor (also known as alpha-1 antitrypsin) and transferrin. Therefore, Fraction IV of the Cohn fractionation process (specifically Fractions $IV_1$ and $IV_4$) can serve as a source of a transferrin-containing liquid preparation in the present invention.

Methods of obtaining partially purified transferrin fractions are known in the art.

For example, U.S. Pat. No. 3,850,903 discloses a method of preparing a protein concentrate that is rich in albumin, transferrin and other $\alpha$- and $\beta$-globulin molecules. Specifically, the '903 patent discloses a Cohn $IV_4$ precipitate that is treated with calcium phosphate followed by selective precipitation with block copolymers of ethylene oxide and polyoxypropylene polymer. As the final product contains a variety of plasma proteins, the '903 disclosure does not provide a method for obtaining highly purified transferrin product per se.

U.S. Pat. No. 4,841,026 describes a method of preparing a sterile, virally inactivated, non-toxic transferrin preparation for use in cell culture systems. The method disclosed therein comprises the saturation of a Cohn fraction containing transferrin with an excess of iron followed by the removal of free iron radicals and unwanted proteins via filtration and ion exchange chromatography. To obtain the final transferrin product, the disclosed process requires a pasteurization period of 10 hours at 60° C.

U.S. Pat. No. 5,041,537 discloses a method of preparing biologically active transferrin, comprising precipitation of $\gamma$-globulin from the Cohn fraction IV, ultrafiltration and adjustment of ionic/protein concentration followed by treatment with specific detergents. The fraction is then subjected to ion-exchange chromatography wherein all of the proteins except the transferrin are adsorbed, i.e., the transferrin is contained in the flow through fraction. The transferrin-containing fraction is subsequently concentrated and filtered sterile.

Methods of inactivating viruses associated with plasma proteins are also known in the art. For example, it is known in the art that plasma proteins can be sterilized using (1) heat-inactivation in the wet and dry states, (2) detergents, and (3) a combination of treatment with $\beta$-propiolactone and ultraviolet radiation. However, plasma proteins are heat-sensitive and therefore must be heat-inactivated in conjunction with stabilizers. Certain stabilizers may act to prevent complete sterilization. Accordingly, sterilization procedures using chemicals and/or radiation are considered preferable for applications requiring complete sterilization. Moreover, it is possible that the heat treatment of transferrin containing preparations will result in the formation of aggregates, thereby potentially hindering the purification and ultimate utilization of the transferrin product. It is also known that viruses can be enveloped or non-enveloped and that viral inactivation methods may be effective for one type of virus, but not another.

For example, U.S. Pat. No. 4,540,573 ("the '573 patent") discloses a general method of obtaining substantially virus-free biologically active protein derivatives that are substantially free of enveloped viruses yet are not denatured by the virus inactivation process. Specifically, a method is disclosed wherein a protein containing composition, e.g. whole blood, is contacted with an organic solvent detergent ("OSD" process) to inactivate enveloped viruses contained therein. The OSD method has the advantage of inactivating hepatitis viruses present in the protein-containing composition without substantial denaturation of the proteins therein. The '573 patent does not disclose the purification of a transferrin-containing fraction.

SUMMARY OF THE INVENTION

It is an objective of this invention to provide a method of producing transferrin products with a high yield and high purity. The method is simple and economical for industrial-scale production of high purity transferrin products.

It is a further objective of this invention to provide a method of preparing highly purified transferrin products that are substantially free of enveloped and non-enveloped viral contaminants.

It is a further objective of this invention to provide a process wherein the transferrin product can be purified and sterilized prior to placement in a final container.

The present invention relates to a method of purifying a transferrin-containing liquid preparation wherein the method comprises starting with a partially purified transferrin liquid preparation. The partially purified transferrin-containing fraction is then concentrated and the ionic strength thereof is lowered. The transferrin-containing fraction is chemically treated to inactivate enveloped viruses. Thereafter, the transferrin-containing fraction is applied to an ion exchange medium in which the transferrin is adsorbed. A fraction comprising transferrin is then eluted from the ion exchange column. In preferred embodiments, the transferrin is saturated with iron and nanofiltered to remove non-enveloped viruses and obtain a sterile product prior to packaging and, if a dry product is desired, the transferrin is lyophilized in a final container. The lyophilized product can be re-constituted at a later time.

DETAILED DESCRIPTION OF THE INVENTION

The starting protein fraction of the present invention is a transferrin-containing protein fraction which has been partially purified, as above-described. Preferably, it is a partially purified Cohn Fraction $IV_1$ and $IV_4$.

The required and optimal process steps of the present invention are as follows:

1. Concentration

The starting material derived from fractions $IV_1$ and $IV_4$ comprising a partially purified liquid transferrin preparation is first concentrated prior to further processing. In a preferred embodiment, the partially purified liquid transferrin preparation is concentrated by tangential flow ultra filtration, such as available from FILTRON.

The partially purified liquid transferrin preparation is concentrated to between 15 mg/ml to 40 mg/ml transferrin or preferably 30 mg/ml. This step can be an optional step when the starting material is of this level of concentration.

2. Diafiltration

After concentrating the partially purified liquid transferrin preparation, the ionic strength of the preparation is decreased to less than 5 mS. Ionic strength is reduced sufficiently so that the transferrin will be adsorbed onto a chromatographic column used during the later chromatography step. In a preferred embodiment, the ionic strength is lowered by diafiltration, for example using a 22.5 mM to 27.5 mM Tris buffer to a conductivity of about 2 mS. In the most preferred embodiment, the ionic strength is lowered using 25 mM Tris buffer, pH 7.5.

3. Chemical Viral-inactivation Treatment

The liquid transferrin preparation is treated with chemicals to inactivate enveloped viruses at a point prior to ion exchange chromatography. In a preferred embodiment, the preparation is treated with known organic solvents with or without surfactants to inactivate viruses. In a more preferred embodiment, the preparation is treated with tri-n-butyl phosphate organic solvent, most preferably, the preparation is treated with 0.3±0.015% tri-n-butyl phosphate and 1.0±0.05% Polysorbate 80 to inactivate viruses.

4. Ion Exchange Chromatography

The preparation is then subjected to ion exchange chromatography wherein the transferrin is adsorbed onto an anion exchange resin. In a preferred embodiment, the anion exchange chromatography resin is DEAE-650 (Toso Hass) or any other DEAE resin (DEAE=diethylaminoethyl). In the most preferred embodiment, the anion exchange chromatography resin is DEAE-650. In a preferred embodiment, the transferrin is eluted with a buffer containing NaCl, such as 30 to 40 mM NaCl in 25 mM Tris buffer. In the most preferred embodiment, the transferrin is eluted with 40 mM NaCl, 25 mM Tris buffer.

5. Second Concentration

The transferrin-containing eluate is then concentrated. In a preferred embodiment, the eluate is concentrated by tangential flow ultra filtration, as in step (1). In a more preferred embodiment, the eluate is concentrated to 9–11 mg/ml of transferrin. In the most preferred embodiment, the eluate is concentrated to about 10 mg/ml of transferrin, of which the total protein content is 95% transferrin, preferably at least 99% transferrin, as described in the product specification in Table 1.

6. Conversion

The transferrin-containing concentrate can then be saturated with iron (conversion from apo-transferrin to holo-transferrin). In a preferred embodiment, the concentrate is saturated with iron by either ferric chloride or ferrous chloride. In a more preferred embodiment, the concentrate is saturated with iron by the addition of ferric chloride so that iron/Tf=1.4 µg/mg to 5.0 µg/mg in the presence of 10 mM to 50 mM sodium bicarbonate, with mixing for 2 to 16 hours. In the most preferred embodiment, the concentrate is saturated with iron by the addition of ferric chloride so that Iron/Tf=3.0 µg/mg in the presence of 10 mM sodium bicarbonate, with mixing for 2 hours.

7. Second Diafiltration

The ionic strength of the saturated product is decreased to less than 5 mS. In a preferred embodiment, the ionic strength of the saturated product is decreased by diafiltration. In a more preferred embodiment, the ionic strength is decreased using 22.5 mM to 27.5 mM Tris buffer. In the most preferred embodiment, the ionic strength is decreased using 25 mM Tris buffer.

8. Sterile Filtration

The saturated product can be further sterilized by filtration. In a preferred embodiment, the saturated product is filtered through a filter that is not more than 0.22 µm. In the most preferred embodiment, the saturated product is filtered through a 0.22 µm filter.

9. Viral Filtration

The saturated product is then nanofiltered to remove viruses. In a preferred embodiment, the saturated product is filtered through a 15 nm or smaller filter. At this time, in the most preferred embodiment, the saturated product is filtered through a 15 nm filter.

10. Lyophilization

The final bulk product may be filled in a final container and lyophilized.

As will be recognized by those skilled in the art, the presently disclosed method provides a simple and economical method of producing highly purified transferrin. The method requires only two major pieces of equipment and three buffers.

EXAMPLES

The invention is illustrated in the following examples.

A. Example 1

A fraction comprising transferrin can be obtained using a process for purifying alpha-1-proteinase inhibitor (hereinafter "$\alpha_1$-PI"). Specifically, $\alpha_1$-PI can be purified from Cohn fractions $IV_1$ and $IV_4$ following the steps described below. The initial quaternary amine anion exhanges (QAE) chromatography step generates a flow through transferrin-containing preparation. Although the preparation is substantially free of albumin, it is not highly purified transferrin and is usually discarded as a waste product. A process for purifying $\alpha_1$-PI and thereby obtaining a starting material for the present invention is as follows:

1. Cohn Fraction $IV_1$ and $IV_4$;
2. Water extraction from Cohn fractions (pH approximately 8.0)
3. Fractionation with 15% PEG and 0.5 mM $ZnCl_2$
4. Supernatant of fractionation of step (3) subject to second fractionation using $ZnCl_2$ (10 mM);
5. Precipitate of step (4) is resolubilized with EDTA;
6. Resolubilized precipitate passed over ion exchange adsorption medium for adsorption of $\alpha_1$-PI.

7. Flow through of ion exchange chromatography of step (6) comprises a partially purified transferrin fraction The partially purified transferrin fraction obtained as above can be further purified using the methods of the present invention to obtain a sterile and substantially virus-free transferrin product.

B. Example 2

A specific example of a process for producing a transferrin-containing preparation for use as the starting material for the present invention herein is the following:

20 kg of Cohn fractions $IV_1$ and $IV_4$ precipitate was resuspended in 180 kg of water for injection ("WFI") at 3.8° C. and the pH was adjusted to 8.94. After the precipitate was resuspended, 242.3 g of Tris, 6.7 kg of 1M NaCl, and 35.4 kg of polyethylene glycol ("PEG") were added and the solution mixed for 60 minutes. Then 2.2 kg of 100 mM $ZnCl_2$ was added and the suspension was adjusted to pH 7.92 and mixed for an additional 60 minutes at 0°–8° C.

The $PEG/ZnCl_2$ precipitate which formed was removed by passing the suspension through a filter press at 0°–8° C. after the addition of 977 g of filtra-Cell BH 20 filter Aid (supplied by Celite of Germany). The filter press was washed before and after filtering with 30 kg of 150 mM NaCl, 15% w/w PEG, 0.5 mM $ZnCl_2$, pH 8.0.

27.8 kg of 100 mM $ZnCl_2$ was added to the supernatant and the solution was adjusted to pH 8. The precipitate which formed in the presence of the $ZnCl_2$ was recovered by centrifugation in a Sharples centrifuge. The $ZnCl_2$ precipitate was re-solubilized in 20 kg of 50 mM EDTA and adjusted to a conductivity of 6.48 mS and to a pH of 7.97.

The re-solubilized $ZnCl_2$ precipitate was then applied to QAE chromatography medium (supplied by Toso Hass) packed into a 20 L column with an internal diameter of 250 cm. The QAE medium was equilibrated at 4° C. with cold water for injection ("CWFI"). The $\alpha_1$-PI was then absorbed into the chromatography medium. The chromatography medium was then washed with 60 L of 50 mM NaCl, 10 mM sodium phosphate, pH 7.92. The partially purified transferrin product is contained in the flow through and wash fractions in the above-described chromatograph step. Although often considered a waste-product, this partially purified transferrin product can be further purified using the methods of the claimed invention herein.

C. Example 3

The following example illustrates the methods of the present invention. A partially purified transferrin fraction derived from Cohn fraction $IV_1$ or $IV_4$ is used as a starting material. The following steps were followed.

2 L of the starting material was concentrated (5×) to approximately 400 ml by tangential flow ultra filtration (UF) with a, 10 to 30 kD nominal molecular weight cutoff (NMWC) membrane. The concentrate was diafiltered with 5 parts to volume ("p.v.") of 25 mM Tris pH 7.5 buffer. This reduced its ionic strength in preparation for ion exchange chromatography. OSD solution with 3% tri-n-butyl phosphate (TNBP) and 10% Polysorbate-80 was added to the product following the viral inactivation protocol disclosed in U.S. Pat. No. 4,450,573 and incubated at 26° C. for 6 hours or more. The final concentrations in the preparation are as follows: TNBP=0.3%, Polysorbate 80=1.0%.

500 ml of DEAE-650 resin packed in a chromatography column was prepared for use by equilibration with the product buffer. 4 column volumes (c.v.) of 25 mM Tris pH 7.5 buffer (2 L), was pumped through the column at a LFR of 0.5 (Runs 1 & 2) and 0.8 (Run 3) ml/cm$^2$/min. These flowrates were maintained for the entire chromatographic step in each run. For run (1), the process chromatography was conducted at 5° C., the remaining runs were conducted at room temperature (23°–25° C.).

330 ml of the transferrin concentrate were loaded onto the column. To remove contaminant proteins and residual OSD the column was washed with 4, 8 and 12 c.v. of 25 mM Tris buffer pH 7.5 buffer for runs 1, 2 and 3 respectively. The column wash eluate was monitored spectrophotometrically at 280 nm and traced on a chart recorder.

Transferrin was eluted using 25 mM Tris pH 7.5 buffer with 40 mM NaCl. To collect the transferrin rich eluate, the eluate was diverted to a collection vessel at the first needle deflection on the chart recorder. Collection of the eluate was stopped when the needle returned to baseline. Approximately 1.6 L of transferrin rich eluate was collected for each run. After recovery of the transferrin, the column was cleaned with 4 c.v. of 25 mM Tris pH 7.5 buffer containing 2M NaCl.

The transferrin eluate was then concentrated by 30 kD ultrafiltration to approximately 300 mL at 10 mg transferrin/mL. To convert the product to holo-transferrin (iron saturated), a solution of 7.2 mM ferric chloride hexahydrate pH 2.7, and a solution of 200 mM sodium bicarbonate pH 8.0 were added to the product to obtain iron/transferrin=3 µg/mg and sodium bicarbonate=10 mM. The product was then incubated at room temperature (23°–25° C.) for 2 hours.

Diafiltration of the product with 6 c.v. of 25 mM Tris pH 7.5 was done to remove excess iron and elution buffer salt. The product was then filtered through a 0.22 µm Millipore 100 cm$^2$ surface area filter at a flow rate of 4 ml/min. This filtration removed bacteria and other micro-particulates in preparation for nano-filtration. The Asahi Planova 15 nm filter was set up for dead-end filtration and the product was pumped through at 0.5 to 1.0 ml/min. This produced a final bulk of about 300 ml.

Final containers of the lot were made by filling 10 ml (100 mg of transferrin) of the final bulk solution into 20 ml vials and lyophilized. The product was lyophilized for a total of 90 hours.

Process optimization experimental data from the chromatography, diafiltration, and conversion steps have led to the definition of the following method. Starting material with Tf concentration of 3 mg/ml is concentrated by UF with a 30 Kd membrane to 15 mg/ml. This is then diafiltered with 5 p.v. of 25 mM Tris Buffer pH 7.5. The concentrate is then treated with OSD following the protocol disclosed in U.S. Pat. No. 4,540,573 and loaded onto a DEAE-650 resin column. Chromatography is conducted at room temperature (23° to 25° C.) at a LFR of 1.0 cm/min. Tf is eluted with 0.04M NaCl 25 mM Tris buffer pH 7.5. Elute is concentrated by UF to a Tf concentration of 10 mg/ml and mixed with iron and sodium bicarbonate solutions to iron/Tf ratio of 3 mg/mg, and bicarbonate of 10 mM at room temperature. The product is then diafiltered with 5 p.v. of 25 mM Tris Buffer pH 7.5. The material is then sterile filtered through a 0.22 µm filter and virus filtered through a 15 nm filter forming the final bulk. 20 ml vials are then filled with 5 ml of 10 mg/ml final bulk and lyophilized over 90 hours following the lyophilization method to form the final container.

The specifications of the product obtained using the disclosed process are listed in Table 1. The transferrin product of the present invention is at least 95% pure and contains 2 µg/mg iron/transferrin molar ratio, with Tf concentration of about 10 mg/ml.

TABLE 1

Product Specification

| | |
|---|---|
| Appearance | Reddish Solid |
| Solubility | <5 min |
| Particulates | Non visible |
| pH | 7.5 ± 0.3 |
| Iron | 1.2 ± 0.2 µg/mg Tf |
| SDS-PAGE | One major band |
| Western Blot | One major band |
| HPLC | >95% area |
| Zinc | 0.8 µg/mg |
| PEG | ≦20 µg/mg Tf |
| TNBP | ≦0.16 µg/mg Tf |
| Tween-80 | ≦30 µg/mg Tf |
| Endotoxin | <1 EU/mg Tf |
| Moisture | <3% |
| Transferrin | 50 mg/vial |
| | 5 mg/ml |

It is understood that the specification and Examples are intended to illustrate but not limit the present invention and that other embodiments within the spirit and scope of the invention will suggest themselves to those skilled in the art.

We claim:

1. A method of purifying transferrin comprising the steps of
   a.) concentrating a partially purified transferrin preparation;
   b.) decreasing ionic strength of the transferrin preparation sufficient for subsequent adsorption of transferrin onto an ion exchange chromatographic medium;
   c.) treating the transferrin preparation prior to the following step (d) with an organic compound for inactivating enveloped viruses;
   d.) subjecting the preparation to an ion exchange chromatography medium, with an ionic strength sufficient to ensure that transferrin is adsorbed;
   e.) eluting transferrin from the ion exchange medium of step (d);
   f.) concentrating the resultant eluate; and
   g.) filtering the concentrated eluate for removing virus particles to obtain a sterile transferrin preparation substantially free of enveloped and non-enveloped viruses.

2. The method of claim 1 wherein the transferrin concentrated eluate from step (e) is saturated with iron.

3. The method of claim 2 wherein the ionic strength of the saturated eluate is decreased.

4. The method according to claim 1 wherein said partially purified transferrin preparation of step (a) is concentrated 5-fold.

5. The method according to claim 1 wherein the ionic strength is decreased by diafiltration.

6. The method according to claim 3 wherein the ionic strength is decreased by diafiltration.

7. The method according to claim 5 wherein the ionic strength of the transferrin preparation is decreased by diafiltration with 25 mM Tris buffer.

8. The method according to claim 6 wherein the ionic strength of the transferrin preparation is decreased by diafiltration with 25 mM Tris buffer.

9. The method according to claim 1 wherein the organic compound for inactivating viruses is an organic solvent detergent.

10. The method according to claim 1 wherein transferrin is eluted in step (d) using 0.04M NaCl, 25 mM Tris buffer.

11. The method according to claim 1, wherein said concentrating in step (a) is carried out by tangential flow ultrafiltration.

12. The method according to claim 1 where said eluate of claim 1 is concentrated to 10 mg/ml protein in step (e).

13. The method according to claim 2 wherein ferric chloride is used to saturate the transferrin preparation.

14. The method according to claim 1 wherein in step (g) the eluate is filtered using a 0.22 µm filter to obtain a sterile transferrin preparation.

15. The method according to claim 1 wherein said filtering of the transferrin preparation in step (g) is carried out using a 15 nm filter to obtain a transferrin preparation that is substantially free of non-enveloped viruses.

16. A transferrin product comprising transferrin that is at least 95% pure, sterile and is substantially virus-free.

17. The transferrin product of claim 16, wherein the transferrin is sterile and substantially free of enveloped viruses.

18. The transferring product of claim 17, wherein the transferrin is sterile and substantially free of non-enveloped viruses.

19. A transferrin product comprising transferrin that is at least 95% pure, sterile and substantially free of enveloped and non-enveloped viruses.

20. The method according to claim 1, wherein said concentrating in step (f) is carried out by tangential flow ultrafiltration.

21. The method according to claim 1, wherein said concentrating in steps (a) and (f) is carried out by tangential flow ultrafiltration.

* * * * *